United States Patent [19]

Dahl et al.

[11] Patent Number: 4,559,951
[45] Date of Patent: Dec. 24, 1985

[54] CATHETER ASSEMBLY

[75] Inventors: Roger W. Dahl, Anoka; David W. Mayer, Bloomington, both of Minn.

[73] Assignee: Cardiac Pacemakers, Inc., St. Paul, Minn.

[21] Appl. No.: 445,240

[22] Filed: Nov. 29, 1982

[51] Int. Cl.[4] .......................... A61B 5/04; A61N 1/05
[52] U.S. Cl. .................................... 128/642; 128/786
[58] Field of Search ................................ 128/784–786, 128/419 P, 642

[56] References Cited

U.S. PATENT DOCUMENTS

| | | | |
|---|---|---|---|
| 3,333,045 | 7/1967 | Fisher et al. | 128/784 |
| 3,367,339 | 2/1968 | Sessions | 128/786 |
| 3,533,403 | 10/1970 | Woodson | 128/419 P X |
| 3,568,660 | 3/1971 | Crites et al. | 128/419 P |
| 3,572,344 | 3/1971 | Bolduc | 128/786 |
| 4,033,355 | 7/1977 | Amundson | 128/786 |
| 4,176,660 | 12/1979 | Mylrea et al. | 128/671 |
| 4,328,812 | 5/1982 | Ufford et al. | 128/786 |
| 4,402,328 | 9/1983 | Doring | 128/785 |

FOREIGN PATENT DOCUMENTS

| | | | |
|---|---|---|---|
| 2494118 | 5/1982 | France | 128/419 P |
| WO80/02231 | 10/1980 | PCT Int'l Appl. | 128/786 |

Primary Examiner—Lee S. Cohen
Attorney, Agent, or Firm—Orrin M. Haugen; Thomas J. Nikolai

[57] ABSTRACT

A catheter assembly designed for long term or short term implantation in an animal body comprising a flexible tube of a biocompatible polymeric material in which plural electrical conductors are helically wound at a predetermined pitch with the conductors being laterally offset from one another and totally buried between the walls of the tube whereby many conductive signal paths can be established through the catheter without increasing its overall diameter. The inclusion of the helically wound conductors in the walls of the tube also allows the torque transfer, flexibility and structural properties to be tailored to fit a variety of applications. Such a catheter may be used as a cardiac pacer lead assembly or as an instrument for carrying out various diagnostic catheterazation procedures.

4 Claims, 11 Drawing Figures

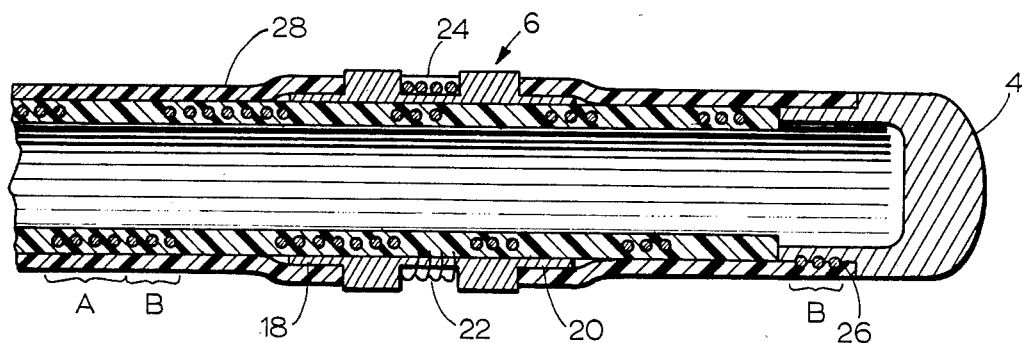
Fig. 4
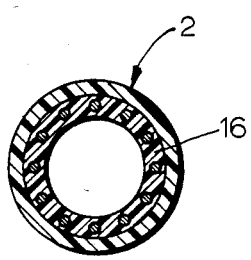
Fig. 2
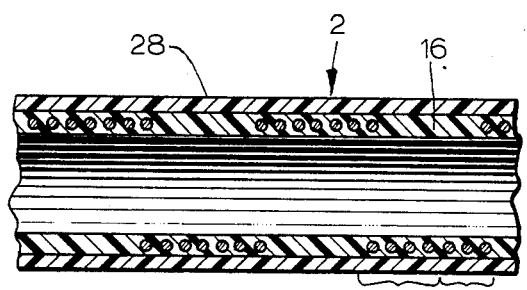
Fig. 3
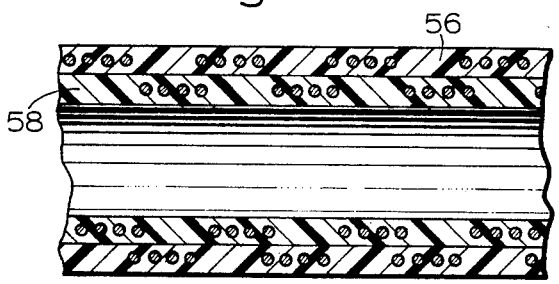
Fig. 11
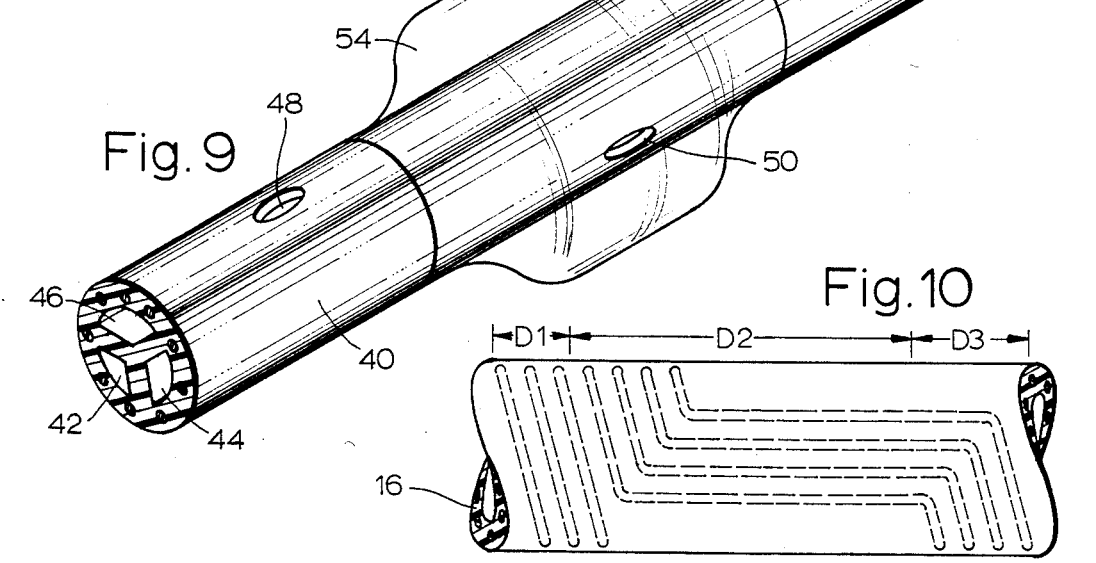
Fig. 9
Fig. 10

CATHETER ASSEMBLY

BACKGROUND OF THE INVENTION

1. Field of the Invention

This invention relates generally to body invasive catheter arrangements including conductive lead assemblies for coupling an electrical device, such as a cardiac pacemaker, to an organ to be stimulated or monitored by conducting signals bi-directionally between the two, to ventriculography catheters for performing various diagnostic procedures, and more particularly to unique catheter constructions which combine multiple electrodes and/or lumens in a small diameter shaft, while maintaining the properties of flexibility, torque control, biocompatibility, resistance to entry of body fluids, and high reliability over prolonged periods of time.

2. Discussion of the Prior Art

Early cardiac pacer systems, by today's standards, were quite primative in that they generally involved a simple asynchronous pulse generator which produced pulses at a fixed rate, the pulses being applied to the heart muscle by way of a single-conductor, unipolar lead and an electrode generaly disposed at the distal tip thereof. Later, bipolar leads were employed in which two electrode surfaces were disposed at the distal end of the lead assembly and the electrical stimulation pulses were applied across these two surfaces. Later yet, so-called demand pacers were introduced in which the electrodes are used for both stimulating the heart muscle and for sensing the natural electrical activity of the heart.

More recently, cardiac pacer systems have become significantly more sophisticated. Pacemaker electronics have improved to the extent that isolated conductive pathways are needed to utilize the accuracy of the sensing circuitry. The energy transmitted via the catheter or lead assembly to artificially pace the heart require, the use of sense circuits in the pacemaker that either momentarily shut off or are blinded during the pacing pulse episode, whereby intermittent sensing of intrinsic heart activity results. There is a need, however, for separate, dedicated conduction pathways so that continuous sensing of cardiac activity can take place.

With the advent of digital, programmable pacemakers constructed using integrated circuit techniques, an increasing number of functions can be performed by the circuits in the implantable pacer. For example, selective pacing and/or sensing in the plural chambers of the heart can be realized. A two-way communication between the implanted pacer and an external programmer/diagnostic device is required in order to take advantage of the capabilities of current pacer designs. Before the conditions being sensed by the implanted pacer can be communicated to the external device, the implanted device must be able to sense and store various physiologic parameters, such as, P-wave and R-wave artifacts, capture verification signals, impedance changes resulting from the beating action of the heart, etc.

As pacer devices become more sophisticated, the lead sets used therewith have also increased in complexity, creating an increasing need to develop multiple sensor mechanisms within a single lead shaft to better represent and respond to physiologic need. With each sensor system, a set of electrically insulated conductors are necessary to insure sensor isolation. In that these leads are often threaded through the body's vascular system, it is imperative that the overall diameter of the lead be minimized. Also, because lives may be at stake, it is essential that the leads perform reliably over prolonged periods in a somewhat hostile environment.

It is also necessary to properly balance the physical properties of the leads to minimize the likelihood of dislodgement from the site of fixation to the organ and to minimize irritation to surrounding tissue such that stimulation thresholds are minimized and remain substantially constant. Thus, it is a desirable property of a pacer lead assembly that it be highly flexible without preferance to any rotational axis while providing a desired degree of torque transmission which, of course, facilitates the routing of the leads through the vascular system during the implantation operation.

Besides implantable pacemaker lead catheters, there are various other types of catheters useful in the diagnosis of organ abnormalities and in the treatment thereof. Angiographic procedures are commonly employed to detect occluded vessels, malfunctioning heart valves and myocardiopathy. These procedures involve the temporary insertion of a tubular catheter having at least one open lumen and the injection of a radio-opaque dye through that lumen while the patient is being examined with a fluoroscope. More sophisticated ventriculographic catheters may include electrodes for pacing and/or measuring electrical field phenomena and/or transducers for monitoring pressure and/or thermistors for measuring temperatures when thermodilution techniques are being employed to measure the stroke volume or other hemodynamic characteristics of the heart.

It may also be desirable, on occasion, to have a cardiac catheter which embodies plural lumens within a single shaft, along with electrical sensing capabilities of the type described above. For example, ports may be positioned along the length of the tubular shaft toward the distal end thereof which communicate with separate lumens extending longitudinally through the shaft so that pressures may be monitored at predetermined points by suitable pressure sensing equipment connected at the proximal end of the catheter. Also, a balloon-type structure may be affixed to the outer wall of the shaft near its distal end, the ballon being inflatable at the proximal end of the catheter shaft by the injection of a suitable fluid through a lumen having a port communicating with the zone covered by the balloon. Such balloons are commonly found on so-called flow-directed catheters in which the balloon helps float the distal end of the catheter through the heart and is used as an anchoring means for holding the catheter in a desired position within the vascular system.

Current technologies involved in both cardiac pacing systems and temporary cardiac monitoring systems have merged, resulting in both short and long term implant configurations of greater complexity and sophistication, with the corresponding overall increase in diameter. This increase in capabilities and sophistication translate to: (1) More electrodes in a greater variety of shapes and/or locations with a corresponding increase in the number of conductors. (2) The incorporation of fluid carrying conduits or lumens and their associated portings; while maintaining the overall diameter, handling characteristics, reliability, and bio-compatability so essential to these applications. A need has therefore arisen for an implantable lead construction that increases the number of conductors and/or fluid channels and/or electrodes without significantly increasing the overall diameter of the catheter or degrading the handling characteristics of the device, i.e., torque control, flexiblity, etc.

SUMMARY OF THE INVENTION

In accordance with the teachings of the present invention, a catheter construction is provided which permits, individually or in combination, a relatively large number of conductor sets, each containing one or more parallel conductors to couple plural electrode surfaces or other electrical devices to appropriate terminal pins located at the proximal end of the catheter, and/or one or more parallel conduits as may be needed to either transport fluids to and/or from a body organ or to accommodate the insertion of a stiffening stylet as is frequently used as a positioning aid during implantation, while maintaining the overall dimensions of the catheter shaft within acceptable limits. Because of the manner in which the individual conductor elements are disposed within this construction, they are effectively isolated one from the other, providing electrical isolation between different electrode systems and fluid-flow isolation beteen ports communicating with the separate conduits, as well as isolation between the electrical and fluid systems.

In accordance with one preferred form of the invention, there is provided a central tube of a predetermined length and wall thickness, which is preferably formed from a polymeric material such as a medical-grade of silicone rubber. Embedded within the cylindrical walls of the tube are a plurality of conductors, each being in the form of a helix with the individual helices being longitudinally offset and electrically isolated by the polymeric material from one another and extending from the proximal end of the lead assembly toward the distal end. Where it is desirable to reduce the electrical resistance of a signal path along the catheter, plural conductor elements may be joined together, thereby effectively increasing the cross-sectional area of the conductor and, accordingly, reducing the electrical resistance measured between their ends. These groups of conductors are then attached to one or more sensing or pacing electrodes which either apply stimulation or pick up electrical signals or signal changes due to physiologic inter-actions. The sensor electrodes are specifically constructed so that when attached to the exterior of the tube, they will not appreciably shift either longitudinally or radially.

It is also a feature of the present invention to provide a still further outer tubular sheath which only partially encompasses each of the surface electrodes disposed on the central tubing layer. This exterior sheath is preferably formed of a polymeric material such as a high performance silicone rubber or polyethylene material having high tear resistance and good biocompatible properties.

It is also a feature of the present invention to provide within the catheter shaft (central tube) one or more inner lumens to allow the receipt of a stiffening stylet, an additional grouping of helically wound conductors and/or fluid transmitting lumens or conduits for injecting dyes, drugs, or monitoring pressures. In those cases where these added features are not desirable, a central core of silicone rubber or like insulating material may be used to provide added stiffness and support to the central tube.

In still a further modification of the invention, it is contemplated that the lumen of the central tube be subdivided so as to provide multiple parallel conduits extending along the assembly's entire length. Such conduits are particularly useful for either passage of a reinforcing stylet or as fluid conduits for injecting and/or removing fluid from the organ as is required when injecting dyes or drugs and/or sampling body fluids or measuring organ pressures.

In yet another arrangement, one or more central conduits running the entire length of the catheter may be used to inflate or deflate a balloon disposed at the distal end of the unit, the balloon being used for routing and then anchoring the tip of the catheter at a desired location or for regulating the flow of fluid in or from the organ.

The invention further contemplates the incorporation of a multiplicity of conductor set wound coaxially within the wall of at least one of the tubes comprising the catheter in the same organ opposite directions and at unequal radii such that each conductor is totally insulated from all other conductors. Such a construction serves to reinforce the walls of the catheter while also increasing the total number of possible conductor sets and the degree of torsional control which can be exercised.

OBJECTS

Accordingly, a primary object of the present invention is to provide a catheter construction possessing a small outside diameter, but still containing a relatively large plurality of insulated and isolated conductors, whereby a number of different electrical signals may be applied to a body organ from a pulse generator or picked up by sensing electrodes at the body organ and conveyed to a remote electronic device.

It is a further object of the present invention to provide a catheter construction of the type described which includes a relatively large plurality of individual groups of electrical conductors while maintaining desired flexibility characteristics.

It is yet a further object of the present invention to provide a lead construction of the type described which includes a plurality of individual fluid conduits extending its entire length for transporting fluids from one end thereof to or from the opposite end.

A still further object of the invention is to provide a catheter structure possessing predetermined characteristics of flexibility, torque transmission, biocompatibility and one or more longitudinally extending lumens, plus a plurality of conductors and electrodes, while maintaining a small outside diameter suitable for transversing the vascular system.

Detailed descriptions of the preferred forms of the invention will now be set forth with reference to the accompanying drawings.

DESCRIPTION OF THE DRAWINGS

FIG. 2 is a cross-sectional view of the catheter assembly taken along the section line 2—2 in FIG. 1;

FIG. 3 is a further cross-sectional view taken along the section line 3—3 in FIG. 2;

FIG. 4 is a further cross-sectional view of the catheter assembly taken along the section lines 4—4 in FIG. 1;

FIG. 9 is a partial perspective view of a ventriculography catheter comprising a third embodiment of the invention;

FIG. 10 illustrates a variation in the winding configuration of the conductors; and FIG. 11 shows still another further alternative construction embodying the present invention.

DESCRIPTION OF THE PREFERRED EMBODIMENTS

Figure 1:
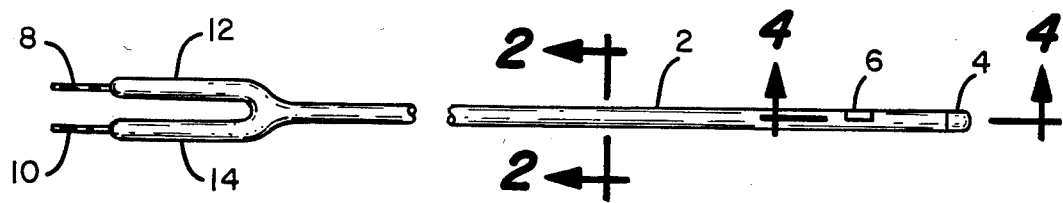
FIG. 1 is a perspective view of a catheter assembly embodying the teachings of the present invention.

Referring first to the embodiment of the invention as reflected in FIGS. 1-5, there is shown a catheter assembly specially adapted for use in connection with a cardiac pacemaker and which is designed for long-term implantation within the body. It comprises an elongated shaft or body portion 2 having a tip electrode 4 at the distal end thereof and located proximally to the tip electrode 4 are one or more surface electrodes 6. Contained within the catheter's shaft 2 is a plurality of electrical conductors leading to appropriate terminal pins, at at 8 and 10, which are shown as exiting from bifurcated segments 12 and 14 of the proximal end of the shaft.

Figure 5:
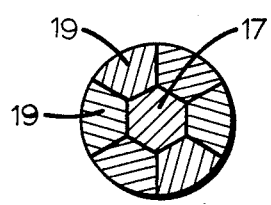
FIG. 5 is a cross-sectional view showing the preferred form of the electrical conductors embodied in the catheter assembly.

As can be seen in the cross-sectional views of FIGS. 2 and 3, the catheter shaft 2 comprises a first elongated tubular plastic member 16 which is preferably formed from a polymeric material such as silicone rubber, but limitation to that particular material is not intended. Buried within the walls of the tubular member 16, i.e., between its respective inside and outside diameters, are a plurality of conductor elements which may be arranged in predetermined groupings, each conducting element of a group being in the form of a helix and with the helices in each group being offset longitudinally with one another. The spacing between individual conductor elements is such that they are electrically isolated one from the other, being insulated by the material comprising the walls of the tubular coating 16. Each of the conducting elements in the groups of conductors may be fabricated as illustrated by FIG. 5 which shows a cross-section of one of the conductors. As can be seen from this figure, it may comprise a central core wire or strand 17, which is preferably a solid strand of silver, this strand being surrounded by a plurality of metal strands 19, which are silver brazed to one another and to the core strand 17. The strands 19 may be stainless steel, elgiloy, an alloy referred to as MP35N or other suitable material. The composite conductor arrangement is subsequently drawn through a suitable die to yield the configuration shown in FIG. 5. Conductors fabricated in this fashion possess the property of unusually high flexibility, fatique resistance and conductivity. One wishing further information on the fabrication of such conductors may refer to the Fisher et al U.S. Pat. No. 3,333,045 entitled "Body Implantable Electrical Conductor" which is assigned to the Central Electrical Company.

For illustrative purposes only, the plural helically wound conductors are arranged in two groups, in FIGS. 3 and 4, with Group A including four conductor elements, and Group B including three conductor elements. Each conductor is shown as being isolated electrically from all others by virtue of being individually and totally surrounded by the plastic comprising the walls of the tubular member 16. For purposes of increased reliability and/or to lower the electrical resistance, individual conductor elements in various groups may be intentionally electrically connected one to the other at their terminations (ends), while being electrically insulated from conductors in neighboring groups. Each conductor in each such group spirals longitudinally down the length of the catheter shaft, terminating in a suitable electrical connector at the proximal end and each group of conductors also being connected in common to an individual surface or tip electrode, such as surface electrode 6 and tip electrode 4 shown in FIG. 4. By providing different surface electrode configurations and/or locations along the catheter's length, it is possible to both monitor electrical artifacts occurring in the organ being catheterized or those electrodes may be used to apply electrical stimulating pulses from an external source to the body organ in question.

In forming the tubular member 16 with the helical conductors buried therein, it has been found convenient to employ a co-extrusion or multiple extrusion process wherein a first tubular extrusion of, say, silicone rubber is wrapped with the appropriate conductors, such as shown in FIG. 3, on predetermined centers using a rotating wire magazine technique just prior to the extrusion of a second outer silicone rubber surface. As the plastic material cures, the finished tubular member 16 has the conductor Groups A and B locked within a silicone rubber wall and completely surrounded with the silicone rubber material.

While only two groups of conductor elements are depicted in FIGS. 3 and 4, those skilled in the art will realize that additional conductors or groups of conductors may be helically wound so as to have the same radius but offset longitudinally by a predetermined pitch. Alternatively, using the co-extrusion process described above, it is also possible to prepare a catheter shaft having a first group of conductors helically wound so as to have a first radius and second groups of conductors helically wound but of a different radius so that they will be coaxially disposed within the walls of the plastic tube 16. This latter approach will, of course, result in a shaft of a greater outside diameter than if the conductor groups all have the same general radius.

With reference now to FIG. 4, the manner in which the surface electrodes may be connected to associated conductor groups will be explained. The surface electrode illustrated generally by numeral 6 in FIG. 4 may comprise a segment of a ring-like tubular piece of conductive material of a predetermined length and having an inside diameter such that it may fit over the outer surface of the tubular structure 16. A medical-grade adhesive may be employed at the interface between the inside surface of the arcuate electrode 6 and the outer surface of the tube 16 to bond the surface electrodes in place. If desired, the surface electrode may be continuous band or ring rather than a radial segment of such a ring. Other known electrode forms such as dots (bailing the end of the wire) and windows that simply expose a portion of the encapsulated conductor are also adaptable to the present invention. Additionally, transducer devices, such as a thermistor may be substituted for the surface electrode 6 and which would have a similar appearance to that in FIGS. 4 and 6.

As can be seen in FIG. 4, the opposed end edges of the surface electrode 6 are of a reduced outside diameter, these end edges being identified by numerals 18 and 20. Also, the surface electrode 6 may have an annular recess 22 formed approximately midway between the opposed end edges, thereby providing a zone in which the plural conductors of a given group of conductors (Group A) traversing the layer 16 may be brought out and electrically connected to the surface electrode. Typically, the individual conductors in a group may be positioned within the recess 22 and then be welded in place to establish a positive mechanical and electrical coupling between the electrode structure and the conductor group. Following the welding operation, the recess may be filled with a polymeric material such as silicone rubber as at 24 to appropriately seal and stabilize the conductors at the point of exit of the conductor groups through the shaft of the catheter assembly 16 at the point where they connect to the surface electrode.

With continued attention to FIG. 4 of the drawings, it can be seen that the plural elements in Group B continue on distally beyond the surface electrode 6 and are welded or otherwise attached to the conductive tip electrode 4 as indicated by numeral 26.

While the structure shown in the embodiment of FIGS. 1 and 4 illustrates only one surface electrode, it is readily apparent that a pacer lead or other like catheter may be configured with more such surface electrodes positioned in a spaced relationship longitudinally or radially around the length of the shaft where the particular application of the catheter assembly dictates. The surface electrodes may comprise a continuous ring or may merely be a portion or segment of such a ring.

In that the surface electrodes may have a reduced thickness proximate to the opposed end edges thereof, a further tubular coating or sheath 28 may be fitted about the catheter body so as to tightly conform to the outer surface of the layer 16 while only partially encompassing the surface electrode 6 in the edge zones 18 and 20 thereof. It has been found that by providing this exterior tubular coating 28 in the manner indicated, it effectively precludes any longitudinal or radial movement of the surface electrode relative to the layer 16. The tubular sheet or sheath 28 may also be fabricated from a medical-grade silicone rubber material in that it tends to be non-thrombogenic and non-fibrosing, thus resulting in a catheter structure which is biocompatible. While silicone rubber is recommended for the sheath 28, other plastic materials having a high tear resistance and high molecular weight relative to the layer 16 may also be used and, hence, limitation to the former is not intended. For example, polyethylene might be used.

In addition to allowing a plurality of separate electrode surfaces to be connected to terminal points at the proximal end of the catheter assembly without increasing the overall outside diameter of the catheter, the interleaved, helically wound conductor groups also can be used to tailor the flexibility and torque transfer characteristics of the catheter. Flexibility is a desired feature of most implantable catheters in that it allows the electrode surfaces to be more accurately and permanently connected to the tissue to be stimulated and/or sensed while the torque transfer characteristics pertain to the ability to route the catheter through the body's vascular system by rotating the catheter shaft as it is advanced. By properly choosing the material comprising the strands of the conductor shown in FIG. 5, and by appropriately determining the number employed and the pitch used in the helices, both flexibility and torque control can be matched to a particular application. By encapsulating the conductors within a polymer, their relationship is fixed. Thus a more controlled or positive feel is achieved because the individual turns can not shift with respect to one another and the thin walled tubes do not twist or kink.

In the embodiment of FIGS. 1 and 4, the lumen of the shaft is vacant and is therefore capable of receiving a stiffening stylet during catheter implantation procedures. In those cases where a stiffening stylet is not to be used with the catheter during implantation, a central core of silicone rubber or like insulating material may be used to provided added stiffness and support to the exterior tube 16.

Figure 6:
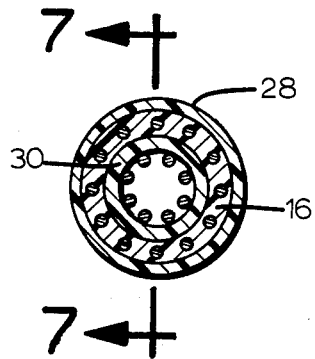
FIG. 6 is a cross-sectional view similar to FIG. 2 but of a catheter assembly in accordance with a second embodiment of the invention.
Figure 7:
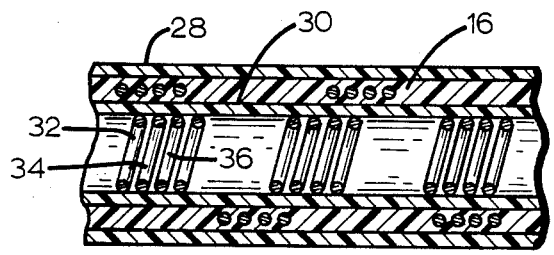
FIG. 7 is a cross-sectional view taken along the section lines 7—7 in FIG. 6.
Figure 8:
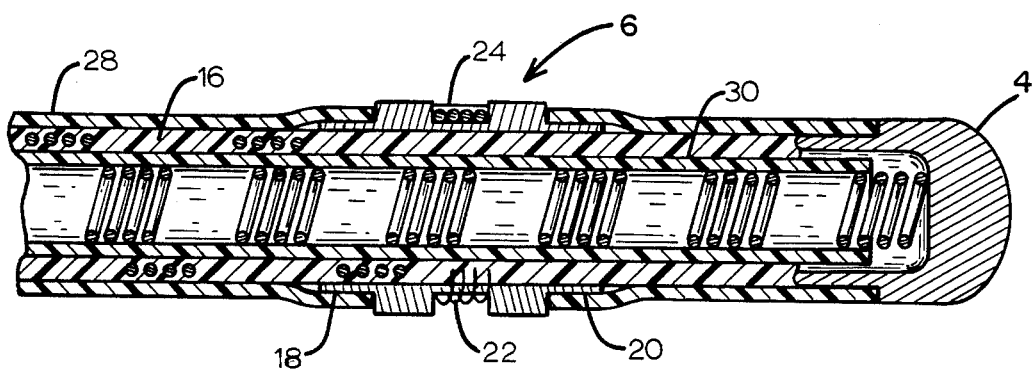
FIG. 8 is an enlarged cross-sectional view of a distal portion of a catheter assembly comprising the second embodiment.

FIGS. 6–8 depict an alternate embodiment of the invention designed for long-term implantation. Here, multiple surface electrodes may be disposed at locations which are spaced longitudinally along the shaft of the catheter and connected to separate contacts or terminals at the proximal end thereof by way of helically wound conductors or groups of conductors embedded in the wall 16. As can be seen in the cross-sectional view of FIG. 6, the lead body or shaft 2 includes an inner elongated tubular member 30 which is preferably formed from a polymeric material such as a high molecular weight polyethylene plastic and, as such, exhibits a high resistance to cutting, gouging, and flaking. The central tubular member 30 extends substantially the entire length of the lead body, but typically only passes through one of the bifurcated branches 12 or 14. The lumen of this central plastic tube 30 is open and inserted within that lumen are a plurality of uninsulated electrical conductors 32, 34, 36, etc. which are each wound in the form of a helix, all of substantially equal radii with the plural helices being laterally offset from one another. These conductors may all be electrically connected in common so as to reduce the overall resistance of this conductor assembly. Typically, each conductor in the group may have the configuration illustrated in FIG. 5, which has already been described hereinabove, or may simply comprise a homogenious single strand of a suitable metal conductor. In addition to reducing the electrical resistance between the tip electrode 4 and its associated proximal terminal pin, by providing plural conductors, all being connected in common, increased reliability due to redundancy is achieved. In that the tube 30 may be fabricated from a high molecular weight polymeric material, for example, polyethylene, the electrical conductors 32–36 may be inserted into the lumen of this tube during manufacture and because the walls defining the lumen are resistant to cutting, scratching or gouging the insertion of the conductors will not result in the generation of tiny particles of plastic scuffed free from the surface of this tube. Another advantage attributable to the multi-layer construction is that any cut created during stringing cannot propagate through the boundary between layers 30 and 16, thus protecting the integrity of the isolation between conductors within tube 16.

The assembly comprising the inner polymeric tube 30, the outer plastic tube 16 with the associated conductor elements buried therein may be fabricated as a single assembly, again through the use of a series of coextrusions. For example, starting with an extrusion of polyethylene or other polymeric material for the layer 30 and followed by an extrusion of silicone rubber of a predetermined thickness, the resulting composite may then be wrapped with the appropriate conductors in a helical fashion along the shaft body using a rotating wire magazine. Immediately following the winding of the conductors, another extrusion of an outer silicone rubber surface is made with that extrusion flowing around and about and intimately joining with the initial extrusion of the silicone rubber layer. Thus, the finished assembly will have a first polymeric layer 30 surrounded by a second silicone rubber layer 16 in which helically wound conductor groups are embedded.

Referring to FIG. 8, it can be seen that the helical conductors, such as 32, 34, and 36 in FIG. 7 which are disposed within the lumen of the central plastic tube 30 are electrically connected to the tip electrode 4. The tip electrode is illustrated as being in the form of a cup which is adapted to receive the conductors and be crimped. The tip electrode 4 may also be of the porous type described in the Amundson Pat. No. 4,156,429, which is assigned to the assignee of the instant application. As is explained in that patent, a porous metal tip enhances tissue ingrowth for more positive lead fixation. Also, while not specifically illustrated in the drawings, flexible tines may be formed near the tip electrode to faciliate its anchoring. While for certain applications a porous tip may be preferred, other pacemaker catheter tip configurations, including positive fixation devices, may be used as well. The manner in which the surface electrodes 6 are secured to the catheter body and electrically joined to predetermined conductor elements in a group has already been explained in connection with the description of FIG. 4 and need not be repeated here. Similarly, the manner in which the outer sheath 28 is employed to increase the stability of the surface electrodes against rotational and longitudinal displacement has previously been explained. It may be observed from FIGS. 6-8, however, that the spiral wound conductors 32-36 define an open center area 38 into which a stiffening stylet may be inserted to facilitate the implantation procedures. The use of a helical coil significantly reduces stylet drag particularly around small bend radii.

FIG. 9 illustrates an embodiment of the invention as applied to a diagnostic catheter as distinguished from a pacemaker lead assembly. As is illustrated, the shaft 40 of the diagnostic catheter is formed from a suitable plastic material and during its extrusion is made to surround a plurality of helically wound electrically conductive elements embedded therein as in the embodiments previously described. Rather than including only a single lumen within the shaft 40, where desired, more than one lumen may be formed during extrusion as indicated by numerals 42, 44 and 46. These lumens may run substantially the entire length of the shaft from the catheter's proximal end toward its distal end where they may be made to communicate with ports formed through the side walls of the shaft as indicated by numerals 48, 50 and 52. For example, the aperture or port 48 may pass through the side wall of the tubular shaft 40 so as to communicate with the lumen 46 while port 50 may communicate with lumen 44 and port 52 with lumen 42. As such, drugs or angiographic dyes may be injected through the catheter to exit at predetermined points near or at its distal end.

The embodiment of FIG. 9 further shows a balloon-type expander member 54 bonded to the outside surface of the shaft and surrounding the port 50. By injecting and removing a fluid from the lumen 44, the balloon element 54 can be made to expand or deflate by virtue of the passage of fluid through the port 50. In carrying out certain monitoring procedures, the ports 48 and 52 disposed on opposite sides of the balloon 54 may be used to sense blood pressure at spaced points along the body of the diagnostic catheter. Similarly, fluids may be drawn through the ports and through the associated lumen for sampling at the proximal end of the catheter.

Where both fluid dynamic properties and electrical sensing are to be achieved from a single catheter, surface electrodes may be added to the embodiment of FIG. 9 in the fashion already described with selected groups of helical conductors embedded in the polymeric material comprising the lead shaft being selectively connected thereto. Furthermore, one or more of the lumens 42, 44 or 46 may be used as a passage for receiving further electrical conductors such as may be used to joint a tip electrode 4 to an external monitoring apparatus (not shown).

FIG. 10 is included to illustrate that the helical pattern of the conductor groups need not be continuous throughout the length of the catheter shaft. The segment of the shaft shown in FIG. 10 includes a plurality of separate, isolated and insulated conductors which may be helically wound over a first longitudinal distance $D_1$ and then undergo a transition in distance $D_2$ and then resume a helically wound pattern over a further distance $D_3$. In the zone $D_2$, rather than being helically wound, the conductors are straight, yet extend longitudinally and remain buried and insulated from each other within the walls of the tubular member 16. By providing the straight segments in zone $D_2$, it has been found to be somewhat easier to isolate one or more conductors for connection to a surface electrode than when the pattern remains a continuous spiral. This facilitates the connection of selective conductor groups to surface electrodes and facilitates the manufacture of catheter assemblies.

It is also contemplated that by selectively controlling the extruder as the outer layer of polymeric coating is being applied over the conductors to be buried, it is possible to leave certain zones void of the outer coating so that the conductors become exposed for attachment to a transducer at that point.

FIG. 11 illustrates still another way in which the present invention may advantageously be utilized. As previously mentioned, by embedding the spiral wound conductors within the walls of polymeric tubes, predetermined tailored torque characteristics may be imparted to the shaft. The embodiment of FIG. 11 shows a first outer tube 56 having one or more groups of conductor elements spirally wound and extending substantially the full length of the lead body. Disposed within the lumen of the first tube 56 is a second tube 58 which also has one or more groups of electrically conductive members embedded in its side walls as illustrated. Here, the conductors within the walls of the outer tube 56 may be joined to surface electrodes in the manner previously described while the electrical conductors contained within the inner tube 58 may be affixed to a positive fixation type electrode such as a corkscrew tip. By using plastic materials having appropriate lubricity characteristics, and because of the torque characteristics tailored into the system by the manner in which the helically wound electrical conductors are embedded in the walls of the respective tubes 56 and 58, it is possible for the physician to rotate the proximal end of the inner tube 58 while holding the proximal end of the outer tube 56 stationary. The rotation of the inner tube, then, can be used to screw the corkscrew-type positive fixation tip into the tissue to be stimulated or sensed.

The invention has been described herein in considerable detail in order to comply with the Patent Statutes and to provide those skilled in the art with information needed to apply the novel principles, and to construct and use such specialized components as are required. However, it is to be understood that the invention can be carried out by other different equipment and devices, and that various modifications, both as to physical details and operating functions can be effected without departing from the scope of the invention itself.

What is claimed is:

1. An intravascular catheter assembly comprising in combination:
   (a) a first extruded flexible plastic tube having at least one lumen longitudinally extending therealong, a proximal end and a distal end, said first tube being formed from a plurality of layered, tubular extrusions, wherein each tubularly extruded layer is extruded over a preceding layer;
   (b) a plurality of electrical conductors integrally contained within the walls of said first tube, each of said electrical conductors being wound in a continuous helix over one of said layers at a predetermined pitch, before extruding the next successive layer thereover, such that the convolutions of each of said helices are bound in noncontacting relation to one another within the walls of said first tube;
   (c) a second flexible plastic tube formed from a plastic material having a high molecular weight relative to the plastic material of said first plastic tube and having an outer diameter which is less than the inner diameter of the lumen of said first flexible plastic tube, said second plastic tube being coaxially disposed within the lumen of said first plastic tube;
   (d) at least one further electrical conductor wound as a helix and disposed within the lumen of said second plastic tube and extending longitudinally from said proximal end to said distal end;
   (e) means attached to each of said conductors at said proximal end for making electrical connections thereto; and
   (f) at least two surface electrodes, one of which has edge portions of a lesser thickness than a center portion thereof and said center portion having an annular recess formed within its exterior surface and wherein an outer tubular sheath formed from a plastic material of a high molecular weight relative to the plastic material of said first plastic tube is mounted over said first tube so as to overlie said edge portions of said one of said surface electrodes to thereby contain said one of said surface electrodes to said first tube and expose said exterior surface of said center portion of said one of said surface electrodes, at least one of said plurality of electrical conductors being electrically coupled to said one of said surface electrodes at said recess, the other of said surface electrodes being positioned at said distal end of said first tube and electrically connected to said further electrical conductor.

2. A catheter assembly as set forth in claim 1 wherein said second plastic tube is movable within the lumen of said first tube.

3. The catheter assembly as in claim 1 wherein the plastic material of said second plastic tube and said outer tubular sheath is polyethylene.

4. A catheter assembly for use with an electrical device in a living animal comprising in combination:
   (a) a first flexible plastic tube having a proximal end and a distal end;
   (b) a plurality of electrical conductor elements helically wound at a predetermined radii and pitch, the convolutions of each of said plurality of electrical conductor elements being axially offset from one another and integrally contained within the walls of said first flexible plastic tube and extending longitudinally therealong from said proximal end toward said distal end;
   (c) an outer tubular sheath formed from a plastic material having a high molecular weight relative to the plastic material of said first plastic tube and concentrically surrounding said first plastic tube;
   (d) means attached to predetermined ones of said plurality of electrical conductor elements at the proximal end of said first plastic tube for making electrical connections to said electrical device; and
   (e) a plurality of tubular ring-like surface electrodes, each of said surface electrodes including edge portions at each end thereof of a lesser thickness than a center portion thereof, said center portion having an annular recess in which predetermined ones of said plurality of conductor elements are attached, and wherein said edge portions are constrained beneath said outer sheath and the exterior surface of said center portion is exposed to body tissue.

* * * * *